United States Patent
Bokade et al.

(10) Patent No.: US 11,773,048 B2
(45) Date of Patent: Oct. 3, 2023

(54) PROCESS FOR THE PREPARATION OF PLATFORM CHEMICALS FROM SUGAR USING ACID CATALYST

(71) Applicant: Council of Scientific & Industrial Research, New Delhi (IN)

(72) Inventors: Vijay Bokade, Pune (IN); Prashant Niphadkar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 17/423,297

(22) PCT Filed: Jan. 15, 2020

(86) PCT No.: PCT/IN2020/050041
§ 371 (c)(1),
(2) Date: Jul. 15, 2021

(87) PCT Pub. No.: WO2020/148779
PCT Pub. Date: Jul. 23, 2020

(65) Prior Publication Data
US 2022/0098140 A1    Mar. 31, 2022

(30) Foreign Application Priority Data
Jan. 16, 2019   (IN) .............................. 201911001842

(51) Int. Cl.
C07C 67/00   (2006.01)
C07C 69/716  (2006.01)
B01J 29/70   (2006.01)

(52) U.S. Cl.
CPC ............ *C07C 67/00* (2013.01); *C07C 69/716* (2013.01); *B01J 29/7007* (2013.01)

(58) Field of Classification Search
CPC ..... C07C 67/00; C07C 69/716; B01J 29/7007
See application file for complete search history.

(56) References Cited

U.S. PATENT DOCUMENTS

2015/0045576 A1*  2/2015  Benecke ................ C07C 67/00
                                                      560/175
2015/0299094 A1* 10/2015  Sawant .................. C07C 67/08
                                                      560/174

FOREIGN PATENT DOCUMENTS

CN           103724201 B  *  5/2016  ............. C07C 67/00

OTHER PUBLICATIONS

CN 103724201 B, Yang Xiaomei et al., Method for preparing ethyl levulinate by catalyzing biomass sugar to be directly alcoholyzed, English Translation, 8 pages (Year: 2014).*
International Search Report dated Jun. 8, 2020 in reference to co-pending Indian Patent Application No. PCT/IN2020/050041 filed Jan. 15, 2020.
Written Opinion dated Jun. 8, 2020 in reference to co-pending Indian Patent Application No. PCT/IN2020/050041 filed Jan. 15, 2020.

(Continued)

*Primary Examiner* — Yate' K Cutliff
(74) *Attorney, Agent, or Firm* — DINSMORE & SHOHL LLP

(57) ABSTRACT

A process is provided for the preparation of value added chemicals such as ethyl levulinate from a glucose or other sugars, catalyzed by a mixture of a Lewis acid catalyst and a Bronsted acid catalyst.

20 Claims, 10 Drawing Sheets

(56) References Cited

OTHER PUBLICATIONS

Jiang, et al., "Direct catalytic conversion of carbohydrates to methyl levulinate: Synergy of solid Brønsted acid and Lewis acid", Applied Catalysis B: Environmental, vol. 220, pp. 589-596, 2018.
Saravanamurugan, et al., "Zeolite Catalyzed Transformation of Carbohydrates to Alkyl Levulinates", Chemcatchem Communications, vol. 5, pp. 1754-1757, 2013.
Chang, et al., "One-pot production of a liquid biofuel candidate—Ethyl levulinate from glucose and furfural residues using a combination of extremely low sulfuric acid and zeolite USY", Fuel, vol. 140, pp. 365-370, 2015.
Li, et al., "Direct transformation of carbohydrates to the biofuel 5-ethoxymethylfurfural by solid acid catalysts", Green Chemistry, vol. 18, pp. 726-734, 2016.

\* cited by examiner (a)

(b)

(c)

(d)

PROCESS FOR THE PREPARATION OF PLATFORM CHEMICALS FROM SUGAR USING ACID CATALYST

CROSS-REFERENCES TO RELATED APPLICATIONS

This application is a national-stage application under 35 U.S.C. § 371 of International Application No. PCT/IN2020/050041, filed Jan. 15, 2020, which International Application claims benefit of priority to Indian Application No. 201911001842, filed Jan. 16, 2019.

TECHNICAL FIELD

The present disclosure relates to a one step process for the preparation of various value added platform chemicals from sugar. The present disclosure more particularly relates to a process for the preparation of value added chemicals such as ethyl levulinate from glucose or other sugars catalyzed by a mixture of a Lewis and Bronsted acid catalyst.

BACKGROUND

Biomass derived biofuels and biochemical is an area where substantial research is in progress. Amongst the various biochemicals, levulinic acid is a molecule of global interest, and its further conversion to alkyl levulinate will find applications as plasticizers, herbicides, perfumery, fuel additives and oxygenators for diesel. Biofuel suffers from a limitation to its use in cold regions due to high freezing point between 3-7° C. The introduction of additives such as ethyl levulinate (EL), which has a freezing point of −79° C., improves properties of biodiesel such as cloud point, pour point, and cold filter plugging point. Further, Ethyl levulinate is a sulphur free additive which can be directly blended with normal diesel or biodiesel or can be used as 100% fuel to replace petroleum diesel.

There are reports of synthesizing EL from sugars, bypassing levulinic acid employing both homogeneous and heterogeneous catalysts. H-USY has been used widely along with a mineral acid and yields are reported up to nearly 52%. The solid loading initially varies between 30-50 g/lt in these reports. While homogeneous catalysts suffer from need for tedious separation processes, heterogeneous catalysts used till date have poor Si:Al ratio or low surface area. Also, some of them exhibit poor catalytic activity in the presence of high concentration of sugars.

The article titled, "Direct transformation of carbohydrates to the biofuel 5-ethoxymethylfurfural by solid acid catalysts" by Hu Li, et al. published in Green Chemistry, 2016, 18, 726-734 reports the conversion of glucose to EMF was examined over several solid acid catalysts in ethanol between 96 and 125° C. Among the catalysts employed, dealuminated beta zeolites [DeAl-H-beta-12.5 (700)] gave a moderate yield of EMF (37%) in a single step catalytic process. A combined catalytic system consisting of H-form zeolite and Amberlyst-15 was found to be more efficient for the transformation of glucose to EMF (46%) via a one-pot, two-step reaction protocol.

The article titled, "One-pot production of a liquid biofuel candidate—Ethyl levulinate from glucose and furfural residues using a combination of extremely low sulfuric acid and zeolite USY" by Chun Chang et al. published in Fuel, 2015, 140, Pages 365-370 reports the conversion of glucose to ethyl levulinate in ethanol medium. Experimental results showed that the combination of extremely low sulfuric acid and zeolite USY can be used as an effective catalytic system for one-pot EL production from glucose. The ethyl levulinate yield of 51.47% from glucose can be obtained at 180° C. and 120 min in the mixed acid system comprising of 0.1% sulfuric acid and 2.0% USY. Combination of extremely low sulfuric acid and USY is efficient for EL production. Higher EL yield of 51.47% from glucose can be obtained in the mixed acid system. Higher EL yield of 18.68% from FRs can be obtained in the mixed acid system.

US2015/0045576 A1 discloses methods have been developed to convert saccharides into value-added products such as alkyl lactates, lactic acid, alkyl levulinates, levulinic acid, and optionally alkyl formate esters and/or hydroxymethylfurfural (HMF). Useful catalysts include Lewis acid catalysts and Bronsted acid catalysts including mineral acids, metal halides, immobilized heterogeneous catalysts functionalized with a Bronsted acid group or a Lewis acid group, or combinations thereof. The saccharides are contacted with the catalyst in the presence of various alcohols.

In prior arts, by using acid catalysts, as the substrate loading is increased, the yield obtained becomes less.

Thus, there is a need in the art to provide a more efficient process for the synthesis of EL. This may be accomplished by making a provision for a more efficient catalytic system to catalyse the conversion of sugars to EL.

Main objective of the present disclosure is to provide a one step process for the preparation of various value added chemicals from sugar.

Another objective of the present disclosure is to provide a one step process for the preparation of various value added chemicals from sugar in presence of a mixture of Lewis and Bronsted acid catalyst.

SUMMARY

Accordingly, the present disclosure provides a one step process for conversion of sugars to corresponding platform chemicals comprising reacting sugar with a physical mixture of Lewis and Bronsted acid catalyst at a temperature in the range of 100-250° C. for 0.5 h to 10 h in alcohol.

In an embodiment, the present disclosure provides a one step process for conversion of sugars to corresponding platform chemicals comprising reacting sugar with a physical mixture of H-USY and $SnO_2$ catalyst at a temperature in the range of 100-250° C. for 0.5 h to 10 h in alcohol wherein the yield of the reaction is in the range of 80 to 85%.

Acronyms
　EL: Ethyl levulinate
　EMF: 5-Ethoxymethyl Furfural
　EL A: Ethyl lactate
　LA: Levulinic acid
　H-USY: Acid form of zeolite
　B/L ratio: Bronsted/Lewis acid ratio
　S/W ratio: Strong to weak acidity ratio
　H-beta: Zeolite type of beta topology
　H-Y: Zeolite type of Y topology
　H-ZSM-5: Zeolite Socony Mobil-5
　SB A-15: SANTA BARBARA AMORPHOUS

DETAILED DESCRIPTION

Figure 1:
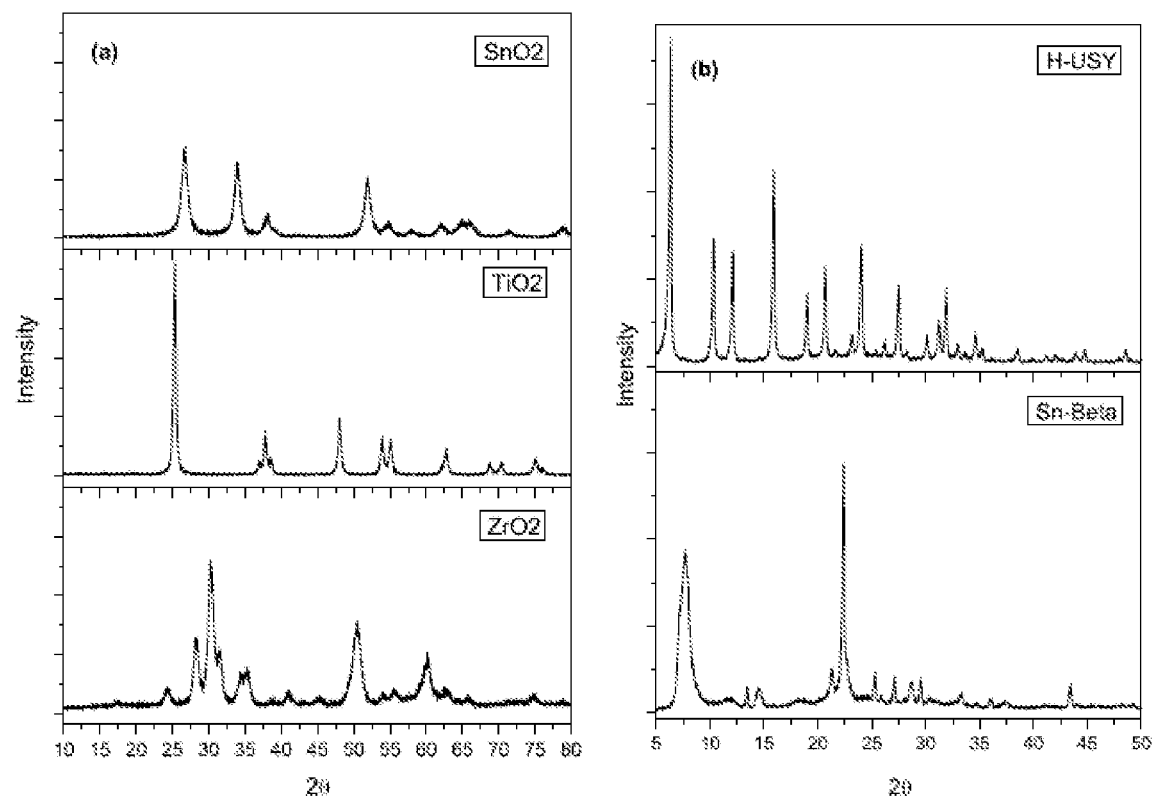
FIG. 1: XRD pattern of (a) $SnO_2$, $TiO_2$, and $ZrO_2$ and (b) H-USY and Sn-beta.

Various embodiments will now be described in detail in connection with certain preferred and optional embodiments, so that various aspects thereof may be more fully understood and appreciated.

The present disclosure provides a one step process for conversion of sugars to corresponding platform chemicals comprising reacting sugar with a physical mixture of Lewis and Bronsted acid catalyst at a temperature in the range of 100-250° C. for 0.5 h to 10 h in alcohol wherein the yield of the reaction is in the range of 80 to 85%.

In an embodiment, the present disclosure provides a one step process for conversion of sugars to corresponding platform chemicals comprising reacting glucose in the presence of a physical mixture of H-USY and SnO$_2$ in the ratio of 5:95 to 95:5 at a temperature in the range of 100-250° C. for 0.5 h to 10 h in ethanol to obtain ethyl levulinate wherein the yield of the reaction is in the range of 80 to 85%.

The sugar is selected from the group consisting of glucose, galactose, fructose, xylose, sucrose, lactose, maltose, trehalose, sorbitol, and mannitol, alone or combinations thereof, preferably glucose.

The Platform chemicals may be defined as value added chemicals derived from natural substrates and are selected from ethyl levulinate, methyl levulinate, 5-HMF, Levulinic acid, Gamma-Valero Lactone; 5-Hydroalkyl furfural preferably 5-Ethoxymethyl furfural, Ethyl Lactate; 5-Methoxymethyl furfural; Methyl Lactate, butyl levulinate, propyl levulinate, hexyl levulinate, octyllevulinate, butyl lactate, propyl lacatate, hexyl lactate, octyl lactate, butyl furfural, propyl furfural, hexyl furfural and octyl furfural.

The 5-Hydroalkyl furfural is Cl-ClO alkyl furfural and is selected from 5-methyl furfural, 5-ethyl furfural, 5-propyl furfural, 5-butyl furfural, 5-pentyl furfural, 5-hexyl furfural, 5-heptyl furfural, 5-octyl furfural, 5-nonyl furfural, 5-decyl furfural. In particularly preferred embodiment, 5-ethyl methyl furfural is used.

The sugar loading for the process of synthesis of platform chemicals may vary between 30-83 g/lt and the catalyst loading is in the range of 30-100% with respect to sugar loading.

The Lewis acid is selected from Sn-beta, TiO$_2$, ZrO$_2$ and SnO$_2$.

The Bronsted acid is selected from H-USY, H-beta; H-Y; H-ZSM-5; all small/medium/large pore zeolites; SB A-15; its hierarchical form; modification by sulphonation/phosphonation and combination of it.

The catalyst for the synthesis of value added chemicals is a physical mixture of 95:5 of H-USY: SnO$_2$, wherein H-USY is commercially available and SnO$_2$ is synthesized as exemplified herein. The surface area of surface area of H-USY is in the range of 600 to 800 m$^2$/gm and Si:Al ratio is in the range of 12 to 30.

The alcohol is selected from methanol; ethanol; propanol; butanol; hexanol; octanol, C1 to C10 alcohols and their mixture.

In the present disclosure, the catalytic direct conversion of glucose to EL without the formation of levulinic acid and aimed to handle higher glucose loading which follows the green chemistry principles such as utilization of renewable materials and omission of derivatization steps and output-led design.

FIG. 1 depicts XRD patterns of (a) SnO$_2$, TiO$_2$, and ZrO$_2$ and (b) H-USY and Sn-beta.

In FIG. 1, (a) illustrates the typical XRD patterns of SnO$_2$, TiO$_2$, and ZrO$_2$. The XRD pattern of SnO$_2$ exhibits diffraction peaks at 2 theta=26.6, 33.9, 38.0, 51.8, 57.9, 62.0, 66.0, 71.3, and 78.7 indicating a tetragonal rutile structure. The XRD pattern of TiO$_2$ shows diffraction peaks at 2 theta=25.4, 36.9, 37.7, 38.5, 48.01, 53.8, 55.03, and 62.07 which confirms the TiO$_2$ anatase structure. The XRD pattern of ZrO$_2$ exhibits diffraction peaks at 2 theta=24.2, 28.2, 30.3, 31.4, 35.3, 40.9, 50.5, 54.1, 55.6, 60.1, 63.0, 65.6, and 74.9, majorly tetragonal phase accompanied with a smaller portion of the monoclinic phase. In FIG. 1, (b) shows a typical XRD pattern of H-USY and Sn-beta for 2 theta range of 5°-50°. The XRD pattern of H-USY and Sn-beta indicates a pure crystalline phase of faujasite and beta.

Figure 2:
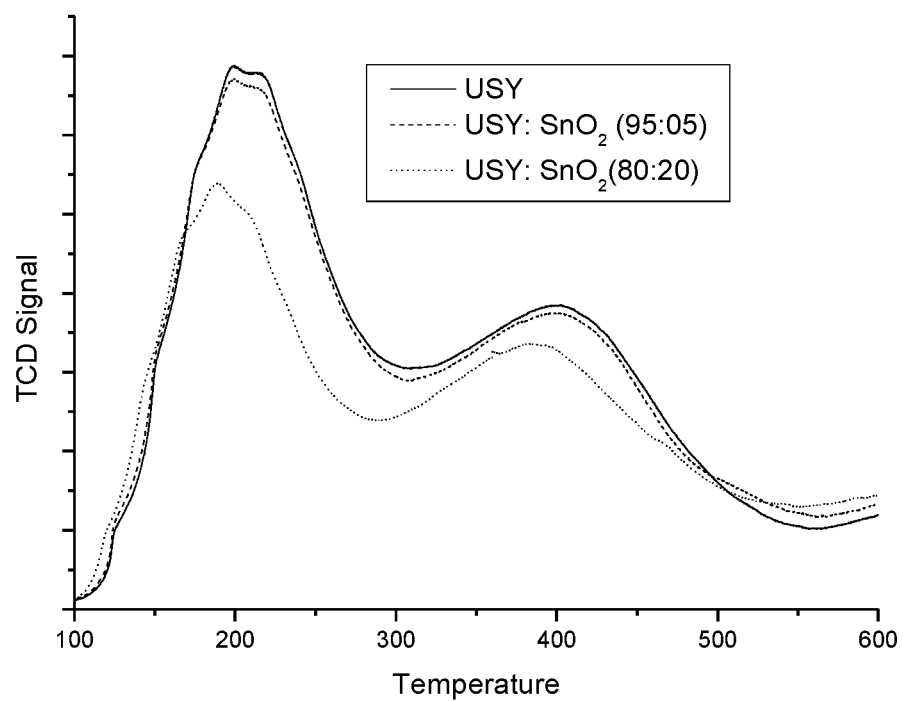
FIG. 2: Ammonia TPD of H-USY, Physical combinations of H-USY and $SnO_2$.

The catalyst comprising a physical mixture of H-USY and SnO$_2$ was characterized, and referring to FIG. 2, the figure illustrates ammonia TPD of H-USY, physical combinations of H-USY and SnO$_2$, as SnO$_2$ mixed with H-USY as a physical mixture. Overall acidity of the catalyst includes combination of weak (100-300° C.) and strong (300-550° C.) acid sites. The acidity is marginally reduced for H-USY: SnO$_2$ of 95:5, whereas it substantially decreased for a mixture of 80:20.

Figure 3:
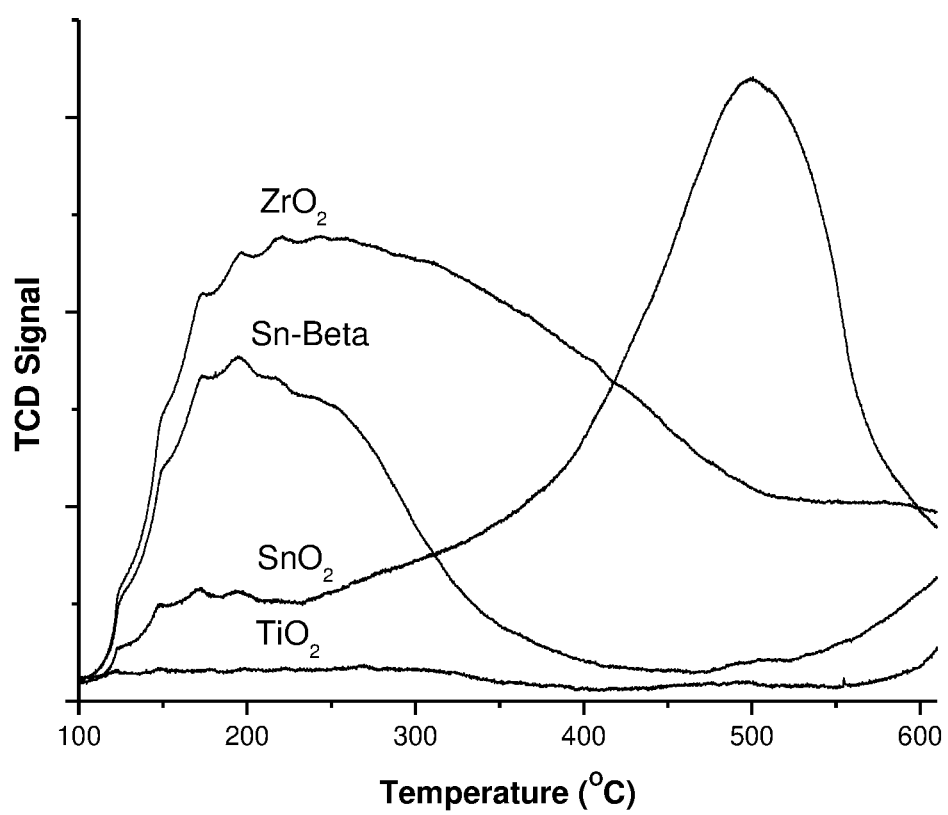
FIG. 3: Ammonia TPD of $SnO_2$, $TiO_2$, and $ZrO_2$ and Sn-beta

FIG. 3 depicts TPD profiles for weak and strong acid sites of the Lewis acidic catalyst such as Sn-beta; ZrO$_2$; TiO$_2$; and SnO$_2$. ZrO$_2$ and Sn-beta showed a single ammonia desorption peak in a temperature range of 100-400° C., which corresponds to weak acidity. The SnO$_2$ displaying two considerable ammonia desorption peaks in 100-250 and 300-600° C. indicate weak and strong acidity, respectively. It is observed that strong acidity has contributed majorly in SnO$_2$ as compared to weak acidity, wherein TiO$_2$ was observed to be the lowest acidic. Among the studied catalysts, only SnO$_2$ was found to have strong acid sites, which are responsible for the reaction of glucose to EL.

Table 1 elaborates on the ratio of strong to weak acidity and specific to its B/L ratio for parent H-USY and physical combinations of H-USY/SnO$_2$. The introduction of SnO$_2$ increases the strong acid sites of the overall combination (HUSY/SnO$_2$) and thereby the strong/weak acidity (S/W) ratio from 1.24 to 2.94, whereas B/L ratio was found to decrease from 0.94 to 0.60. This confirmed that by the introduction of SnO$_2$, the contribution of Lewis acid sites increases, which is especially required for isomerization of glucose to fructose and partly for the ethanolysis step. Among the Lewis acid catalysts, the total acidity trend is ZrO$_2$ (0.46 mmol/g)>SnO$_2$ (0.37 mmol/g)>Sn-beta (0.26 mmol/g)>TiO$_2$ (0.05 mmol/g). However, the ZrO$_2$ has weak Lewis acid sites, whereas SnO$_2$ has strong acid sites.

TABLE 1

Acidity Properties of Different Catalyst

| Sr. No. | Catalyst | Strong/weak | B/L | Total acidity (mmol/g) |
|---|---|---|---|---|
| 1 | H-USY | 1.24 | 0.94 | 0.74 |
| 2 | H-USY/SnO$_2$ (95:05) | 1.30 | 0.75 | 0.70 |
| 3 | H-USY/SnO$_2$ (80:20) | 2.94 | 0.60 | 0.64 |
| 4 | Sn-beta | | | 0.26 |
| 5 | SnO$_2$ | | | 0.37 |
| 6 | TiO$_2$ | | | 0.05 |
| 7 | ZrO$_2$ | | | 0.46 |

Figure 4:
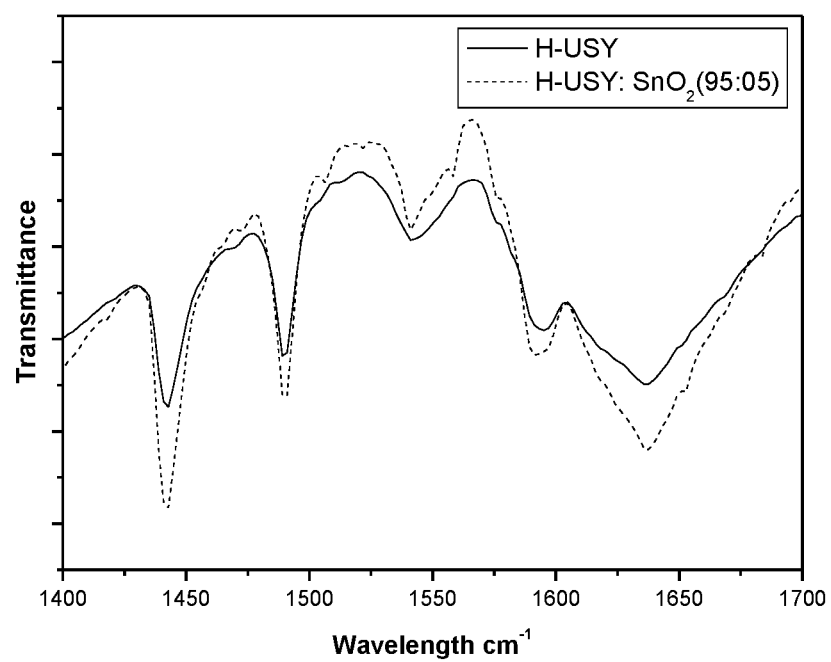
FIG. 4: Pyridine IR of H-USY and physical combination of H-USY:SnO$_2$ (95:05).

FIG. 4 depicts Pyridine IR of H-USY and physical combination of H-USY:SnO$_2$ (95:05). Pyridine-IR spectra exhibits Lewis acidity at 1443 cm$^{-1}$ and Bronsted and Lewis at 1490 and 1544 cm$^{-1}$ for only Bronsted acidity, respectively.

Figure 5:
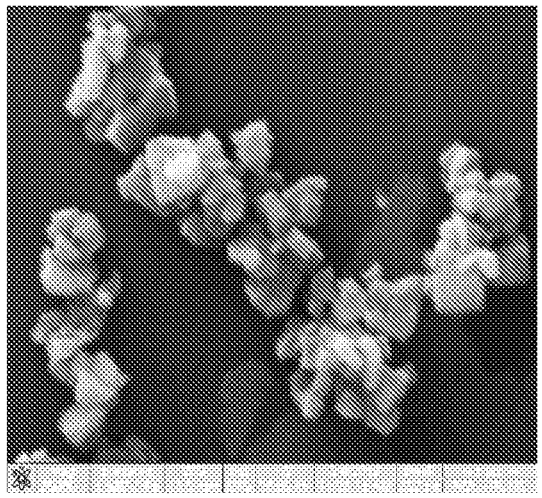
FIG. 5: SEM images of (A) H-USY, (B) SnO$_2$ (C) Physical combination of H-USY:SnO$_2$ (95:05) (D) Physical combination of H-USY:SnO$_2$ (80:20)
Figure 5:
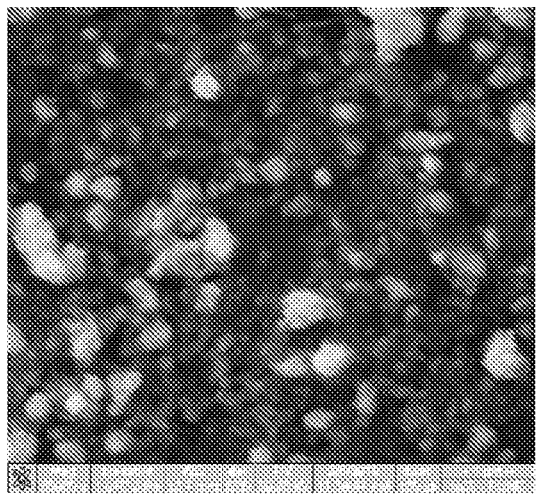
Figure 5:
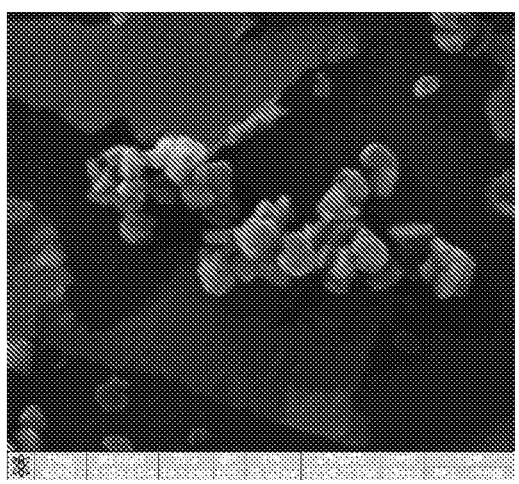
Figure 5:
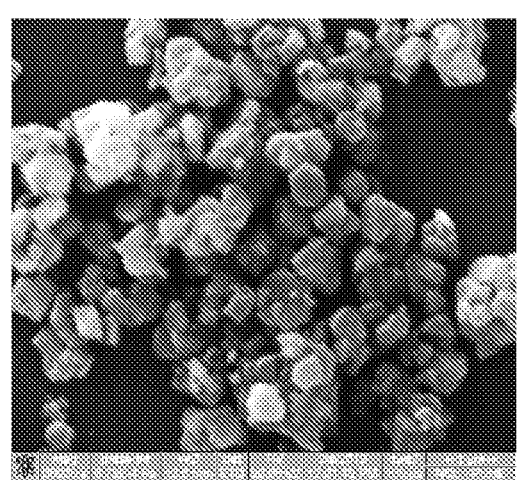

The size and morphology of H-USY and SnO$_2$ and the physical combination of H-USY and SnO$_2$ were studied using SEM, and the SEM images are provided in FIG. 5. H-USY exhibited cubic- and hexagonal-shaped particles having a size of 0.5-0.75 mm, whereas SnO$_2$ showed agglomerates of spherical-shaped particles with a size of around 0.1 mm. The physical combination of H-USY and SnO$_2$ showed a mixed morphology of H-USY and SnO$_2$.

The structural properties of H-USY and a physical combination of H-USY and SnO$_2$ are provided in Table 2. In comparison with H-USY, the BET surface area of the physical combination of H-USY and SnO$_2$ was observed to be in a decreasing trend with a percent increase in SnO$_2$ concentration. Whereas pore volume and pore diameter were observed to be constant throughout which it reveals that additional SnO$_2$ in physical combination does not hinder or block the pores of H-USY.

From Table 2, it is observed that, the combination of H-USY/SnO$_2$ (80:20) gives a maximum EL yield of 57% (Table 2, entry 6) as compared to plain HUSY (45%). This enhancement of EL yield is due to additional strong Lewis acid sites generated from SnO$_2$. Among Lewis acidic catalysts, SnO$_2$ is found to be more active than others because SnO$_2$ has more contribution of strong Lewis acid sites than weak, whereas others have only weak Lewis acidity (FIGS. 3, 4, and Table 1). In all cases, the EMF formation is in the range of 3-10%, whereas ELA is in the range of 1-4% except plain Sn-beta (18%) (Table 2, entry 2), which is the Lewis acidic catalyst with the structure of beta, which leads to the formation of ELA by retro-aldol condensation reaction (Lewis acidic reaction).

TABLE 2

Preparation of platform chemicals using different Catalyst

| | Catalyst | % EL | % EMF | % ELA |
|---|---|---|---|---|
| 1 | H-USY | 45 | 3 | 0 |
| 2 | Sn-Beta | 0 | 10 | 18 |
| 3 | H-USY + Sn-Beta | 51 | 8 | 4 |
| 4 | H-USY + TiO$_2$ | 40 | 5 | 0.4 |
| 5 | H-USY + ZrO$_2$ | 48 | 6 | 1 |
| 6 | H-USY + SnO$_2$ | 57 | 6 | 1 |

In other Lewis acidic catalysts, the surface reaction is predominant as it is a structure-less material. Overall, the combination of H-USY/SnO$_2$ (80:20) having higher S/W ratio (2.94), with low B/L ratio (0.60) having strong Lewis acidity because of the presence of SnO$_2$ reflected to be highly active with the EL yield of 57% at the minimum formation of EMF (6%) and ELA (1%).

Table 2 confirmed that the EMF formation is <10% in all of the combination of H-USY (80%) with other L acidic catalysts (20%) such as TiO$_2$; SnO$_2$; Sn-beta; and ZrO$_2$.

Figure 6:
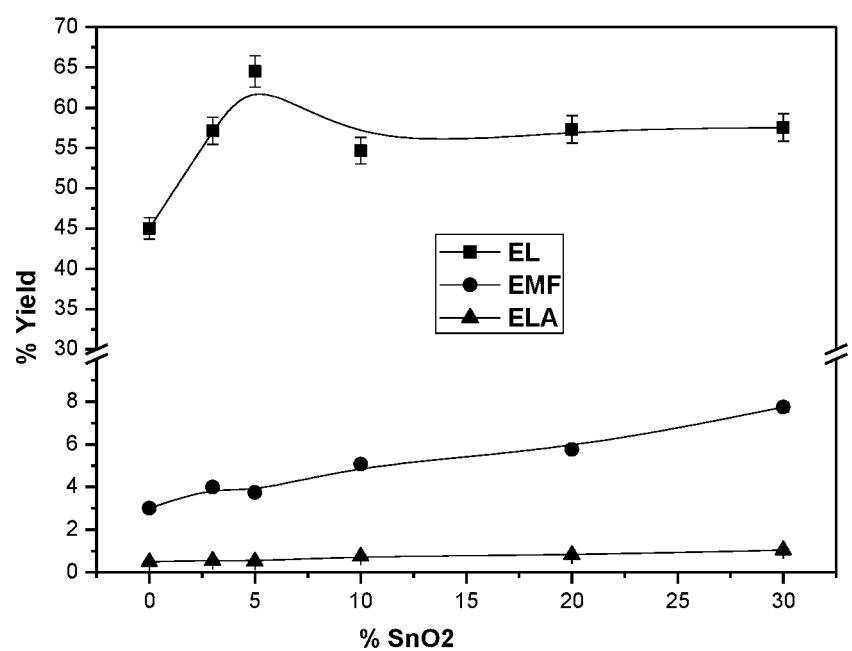
FIG. 6: Effect of % SnO$_2$ on yields of (a) EL, (b) intermediate sugars (mannose, glucosides, and fructosides), (c) EMF, (d) ELA catalyzed by H-USY: SnO$_2$, glucose concentration=50 g/L, catalyst loading=50% wrt glucose concentration, 12 mL of ethanol, 800 rpm, 160° C., and 3 h.

From FIG. 6 it is observed that the concentration of strong Lewis acid sites in combination with H-USY and SnO$_2$ changed with an increase in SnO$_2$ percent from 0 to 30%. In case of zeolite H-USY, an EL yield of about 45% was obtained along with intermediate sugars, whereas when the reaction is catalyzed with a combination of H-USY and SnO$_2$ (97:03), the EL yield is observed to be increased up to 57%. With the addition of SnO$_2$, strong Lewis acid sites (FIGS. 3 and 4) are utilized to convert formed glucosides to fructosides, which leads to the formation of EL. As the quantity of SnO$_2$ is increased from 3 to 5%, a sharp increase in EL yield from 57 to 64% was noticed, which is governed by the conversion of remaining available glucosides to fructosides. Further increment in SnO$_2$ to 7% EL yield is observed to be identical to that of 5%. At 10% SnO$_2$ loading, the EL yield decreased to 55% with a slight increment in intermediate sugars. A drop in the EL yield might be because of insufficient amount of Bronsted acid sites of HUS-Y in combination with SnO$_2$ (90:10).

Above 10% SnO$_2$ loading, overall Bronsted acidity decreases because of the lesser contribution of H-USY in the combination, which promotes the marginal increment in the EMF formation from 5 to 8%; however, further conversion of EMF to EL is observed to be limited because of the less availability of Bronsted acidity. Moreover, almost identical ELA formation of 1% is found throughout different concentrations of SnO$_2$. The increase in EL yield with the addition of SnO$_2$ is mainly because of the improvement in Lewis acidity, especially strong Lewis acidity which is responsible for enhancement in the rate of isomerization reaction than plain H-USY, thereby increasing the overall rate of reaction and so the yield. However, excess strong Lewis acidity is also not advantageous because it reduces the Bronsted acidity which is required for dehydration of fructosides to EMF and alcoholysis of EMF to EL reaction. Thus, a proper combination of B/L (0.75) and S/W (1.30) (Table 1) is critical for this reaction, which suits well with 5-7% of SnO$_2$ and H-USY having properties such as surface area=780 m$^2$/g and Si/Al=15.

Figure 7:
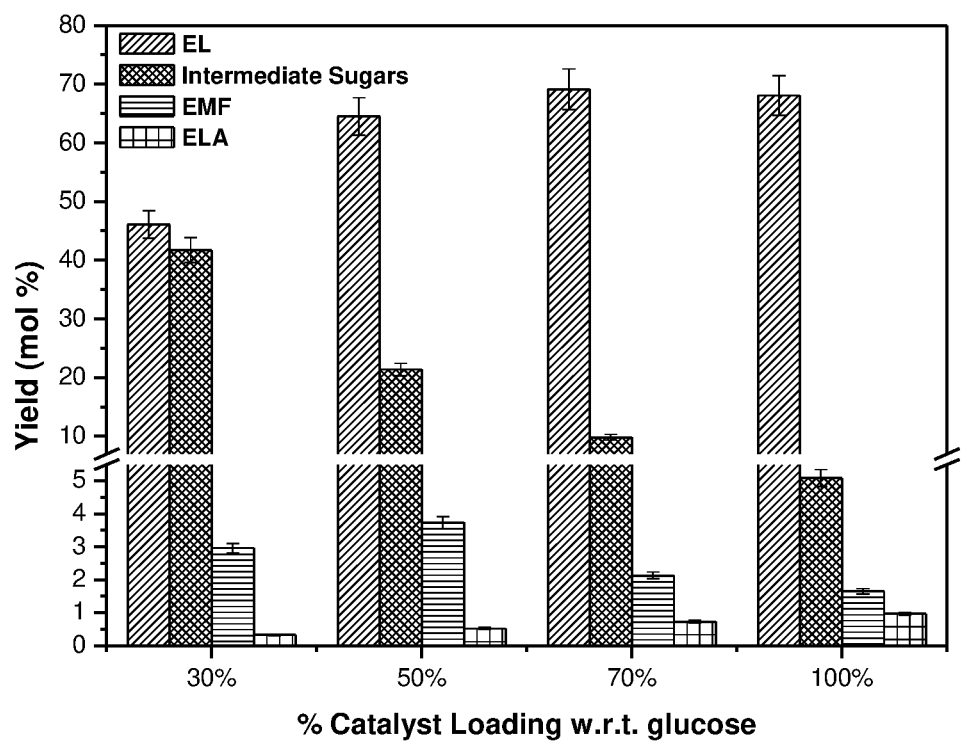
FIG. 7: Effect of catalyst (H-USY+SnO$_2$) loading with respect to glucose concentration on yields of EL, intermediate sugars, EMF, and ELA catalyzed by H-USY/SnO$_2$ (95:05), glucose concentration=50 g/L, 12 mL ethanol, 800 rpm, 160° C., and 3 h.

FIG. 7 depicts the effect of catalyst loading HUSY/SnO$_2$ (95:05) on product yield. As catalyst loading increases from 30 to 50%, a sharp increase in the EL yield from 46 to 65% is observed.

Figure 8:
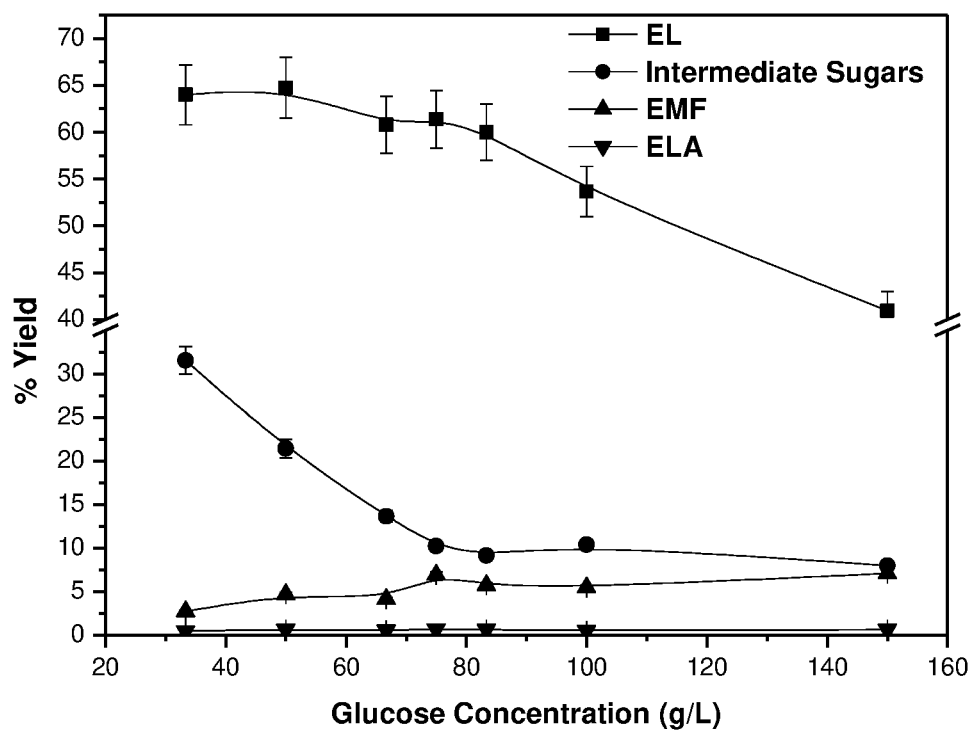
FIG. 8: Effect of variation in glucose concentration on % yield of EL, intermediate sugars, EMF, and ELA catalyzed by H-USY/SnO$_2$ (95:05), catalyst loading=50% with respect to glucose concentration, 12 mL ethanol, 800 rpm, 160° C., and 3 h.

FIG. 8 depicts the effect of glucose concentrations on the yield of EL, EMF, and ELA. Up to a glucose concentration of 50 g/L, keeping the ethanol concentration in a reaction medium the same, the EL yield is observed to be identical at 65%. Above 50 g/L glucose concentration, the marginal decrease in EL yield from 65 to 60% is observed up to 83 g/L glucose concentration. Above 83 g/L glucose concentration, the EL yield is decreased to 41% at 150 g/L glucose concentration. The increasing trend of EMF formation and the identical formation of ELA is noted as glucose concentration increases. Also, the decreasing trend of intermediate sugar formation with the increasing glucose concentration in reaction mixture is noticed.

Figure 9:
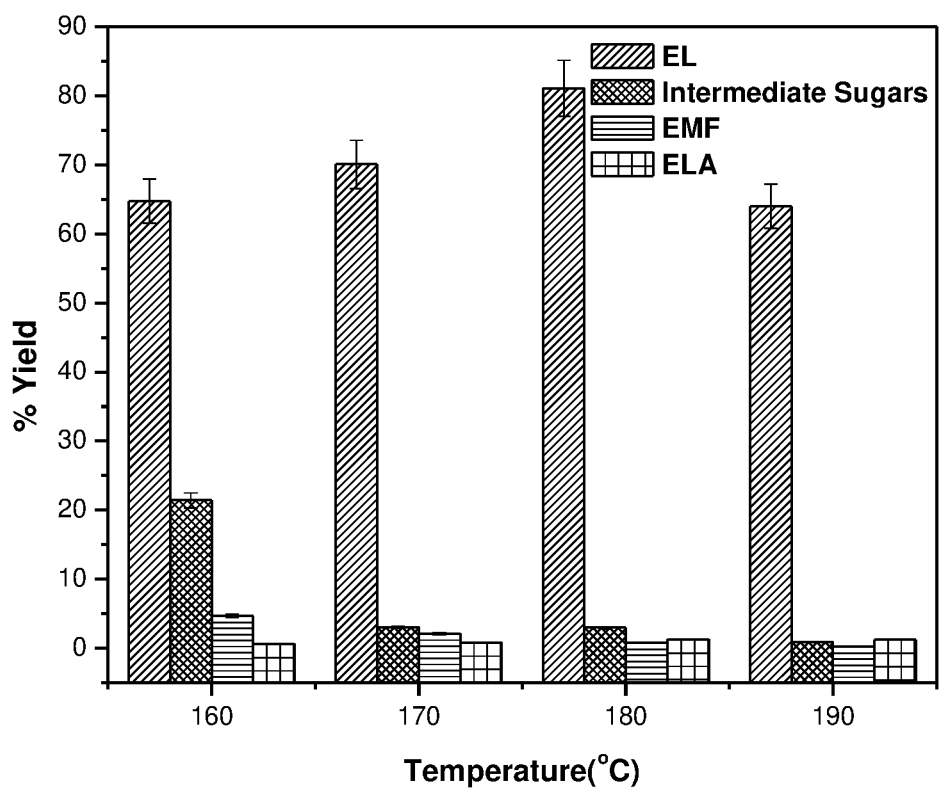
FIG. 9: Effect of temperature on yields of EL, intermediate sugars, EMF, and ELA catalyzed by H-USY/SnO$_2$ (95:05), glucose concentration=50 g/L, catalyst loading=50% with respect to glucose concentration, 12 mL ethanol, 800 rpm, and 3 h.

FIG. 9 depicts the effect of temperature on % yield of EL, EMF, and ELA from 160 to 190° C. As the temperature increases from 160 to 180° C., with decrement in intermediate sugars, the EL yield is observed to be increased from 65 to 81%, which is substantial and highest so far.

Figure 10:
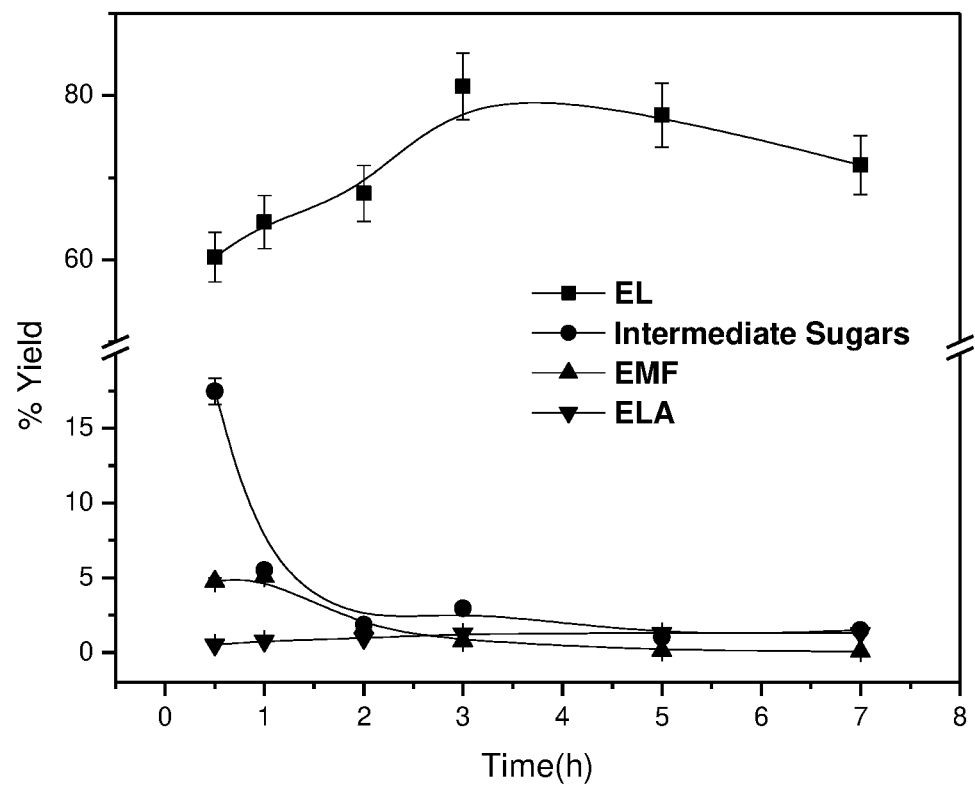
FIG. 10: Effect of time over % yields on EL, intermediate sugars, EMF, and ELA catalyzed by H-USY/SnO$_2$ (95:05), glucose concentration=50 g/L, catalyst loading=50% with respect to glucose concentration, 12 mL ethanol, 800 rpm, and 180° C.

FIG. 10 depicts the effect of time from 0.5 to 7 h on the yield of EL, EMF, ELA, and intermediate sugars. Up to a reaction time of 3 h, the EL yield is found to be on an increasing trend from 60 to 81% with a decrease in intermediate sugars and EMF along with a slight increase in ELA formation. At higher temperature of 180° C., when the reaction time prolonged for more than 3 h, the substantial decrease in the EL yield from 81 to 73% was observed.

TABLE 3

Effect of catalyst (HUSY + $SnO_2$) loading w.r.t. glucose concentration on yields of EL HMF, ELA Catalyzed by H-USY:$SnO_2$ (95:05)

| Catalyst Loading (%) | EL Yield (mol %) | EMF Yield (mol %) | ELA Yield (mol %) |
|---|---|---|---|
| 30% | 46.08 | 2.96 | 0.33 |
| 50% | 64.5 | 3.74 | 0.52 |
| 70% | 69.14 | 2.13 | 0.73 |
| 100% | 68.06 | 1.65 | 0.97 |

Reaction conditions: glucose concentration = 50 g/L, 12 mL ethanol, 800 RPM, 160° C., 3 h

TABLE 4

Glucose concentration: Effect of variation in glucose concentration on % yield EL, EMF and ELA catalyzed by H-USY:$SnO_2$ (95:05)

| Glucose concentration (g/L) | EL Yield (mol %) | EMF Yield (mol %) | ELA Yield (mol %) |
|---|---|---|---|
| 33.33 | 64 | 2.71 | 0.47 |
| 50 | 64.75 | 4.67 | 0.63 |
| 66.66 | 60.8 | 4.13 | 0.56 |
| 75 | 61.37 | 6.92 | 0.65 |
| 83.33 | 60 | 5.7 | 0.62 |
| 100 | 53.66 | 5.45 | 0.52 |
| 150 | 40.94 | 7.1 | 0.62 |

Reaction condition: catalyst loading = 50% w.r.t. glucose concentration, 12 mL ethanol, 800 RPM, 160° C., 3 h

TABLE 5

Effect of Temperature on yields of EL, EMF, ELA Catalyzed by H-USY:$SnO_2$ (95:05)

| Temperature | EL Yield (mol %) | EMF Yield (mol %) | ELA Yield (mol %) |
|---|---|---|---|
| 160 | 64.75 | 4.67 | 0.63 |
| 170 | 70.09 | 2.08 | 0.85 |
| 180 | 81.1 | 0.77 | 1.26 |
| 190 | 64.02 | 0.225 | 1.2 |

Reaction condition: concentration = 50 g/L, catalyst loading = 50% w.r.t. glucose concentration, 12 mL ethanol, 800 RPM, 3 h

TABLE 6

Effect of time over % yield EL, EMF and ELA catalyzed by H-USY:$SnO_2$ (95:05)

| Time | EL Yield (mol %) | EMF Yield (mol %) | ELA Yield (mol %) |
|---|---|---|---|
| 0.5 | 60.32 | 4.76 | 0.51 |
| 1 | 64.6 | 5.07 | 0.77 |
| 2 | 68.07 | 1.63 | 0.95 |
| 3 | 81.1 | 0.77 | 1.26 |
| 5 | 77.6 | 0.125 | 1.28 |
| 7 | 71.55 | 0.075 | 1.285 |

Reaction condition: glucose concentration = 50 g/L, catalyst loading = 50% w.r.t. glucose concentration, 12 mL ethanol, 800 RPM, 180° C.

The reusability of catalyst H-USY (95%) and $SnO_2$ (5%) was investigated over the identical optimized conditions (glucose concentration=50 g/L, 50% catalyst loading, 180° C., 3 h).

After the first run, the catalyst was washed with acetone and then calcined at 550° C. and then was reused for the next reaction. The catalyst was observed to be active up to 4 runs with almost constant glucose conversion of 90% (±3%) and EL yield of 81% (±3%) over a synergetic combination of H-USY and $SnO_2$.

In various embodiments, the H-USY used has the following properties: surface area 780 $m^2$/g; Si/Al ratio=15; strong to weak acidity of 1.24, and Bronsted to Lewis acidity ratio of 0.94, with total acidity of 0.74 mmol/g of catalyst. These properties of H-USY are not reported for glucose to ethyl levulinate. In various embodiments, the, optimum catalyst is a physical combination of H-USY (95%)+$SnO_2$ (5%) which changes the properties of the overall invented catalyst to: strong to weak acidity ratio of 1.30; Bronsted to Lewis acidity ratio of 0.75; total acidity of 0.70 mmol/g of catalyst. This combination is not reported for glucose to ethyl levulinate so far.

This particular combination of catalyst can handle glucose concentration up to 50 gm/L (50 gm of glucose in 1 L of ethanol), which is higher than reported. Reported optimum glucose concentration is 20 g/L. This means that, present catalyst can handle more substrate concentration with improved ethyl levulinate yield of 81%, which increases the overall process productivity.

EXAMPLES

Following examples are given by way of illustration therefore should not be construed to limit the scope of the disclosure.

Procurement Raw Materials:

Zeolite H-USY: The commercial H-USY zeolite (CBV 720) with Si/Al=15 and surface area=780 $m^2$/g was procured from zeolyst Internationals, Netherlands Example 1: General Example for Preparation of Ethyl Levulinate Glucose concentration in ethanol from 33.33 g/L with physical mixture of H-USY and $SnO_2$ catalyst loading of 70 wt % with respect to glucose was subjected to thermal treatment at temperature range of 160° C. for different time span of 7 h. All the reactions were carried out at 800 RPM to overcome external mass transfer limitations during the reaction. The reaction mixture was cooled in cold water bath to reach 30 degree followed by separation from the catalyst by centrifugation. Supernatant reaction mixture was diluted with ethanol and injected into Gas Chromatography (GC)

system (chemito-1000) equipped with TR capillary column (30 mm×0.32 mm×0.25 mm) and Flame Ionization Detector with carrier gas $N_2$ with flow rate 1.0 mL min$^{-1}$. Injection port temperature, oven temperature and detector temperature were programmed at 230° C., 50 to 280° C. with heating rate 20° C. min$^{-1}$ and 260° C. for feed and product analysis. Yields of EL, EMF and ELA are calculated by following equations:

% Yield of EL=(Moles of EL/Moles of Glucose)
*100%

Yield of EMF=(Moles of EMF/Moles of Glucose)
*100%

Yield of ELA=(Moles of ELA/Moles of Glucose)
*100

Example 2: Preparation of $SnO_2$ 50 g of CTAB (cetyltrimethyl ammonium bromide) was added to 500 mL DM water and then stirred for 1 hour. Another aqueous solution of 50 g $SnCl_4·5H_2O$ was prepared in 500 mL water under constant stirring. Homogenous solution of 80 mL ammonium hydroxide in 80 mL DM water was mixed with previously prepared CTAB solution. Aqueous solution of SnCl was added in CTAB and $NH_4OH$ mixture. After complete addition of $SnCl_4·5H_2O$ solution, the slurry was stirred for 4 h and afterwards kept for aging for 48 h at 30 degrees temperature. Slurry was then filtered and washed with DM water and acetone. Wet cake was kept in oven at 100° C. for 12 h and then calcined at 550° C. for 12 h with rate of 1° C./min.

Advantages
1. Green and eco-friendly process
2. Simple process to synthesize catalyst
3. Higher yields of value added platform chemicals
4. Catalyst can tolerate higher concentration of sugars
5. Catalyst can be used for any type of sugars; C1-C10 alcohols and their mixtures.

The invention claimed is:

1. A one-step process for converting sugars to platform chemicals, the one-step process comprising reacting a sugar with a physical mixture of a Lewis acid catalyst and a Bronsted acid catalyst at a temperature from 100° C. to 250° C. for 0.5 h to 7 h in an alcohol to obtain the platform chemicals with a reaction product yield from 60% to 85%, wherein:
the Lewis acid catalyst comprises Lewis acid catalyst particles;
the Bronsted acid catalyst comprises Bronsted acid catalyst particles; and
the physical mixture of the Lewis acid catalyst and the Bronsted acid catalyst comprises a combination of the Lewis acid catalyst particles and the Bronsted acid catalyst particles showing a mixed morphology.

2. The one-step process of claim 1, wherein the sugar is selected from the group consisting of glucose, galactose, fructose, xylose, sucrose, lactose, maltose, trehalose, sorbitol, mannitol, and combinations thereof.

3. The one-step process of claim 1, wherein the platform chemicals are selected from the group consisting of ethyl levulinate, methyl levulinate, 5-HMF, levulinic acid, gamma-valerolactone, 5-hydroalkyl furfural, 5-ethoxymethyl furfural, ethyl lactate, 5-methoxymethyl furfural, methyl lactate, butyl levulinate, propyl levulinate, hexyl levulinate, octyl levulinate, butyl lactate, propyl lactate, hexyl lactate, octyl lactate, butyl furfural, propyl furfural, hexyl furfural, and octyl furfural.

4. The one-step process of claim 1, wherein the sugar is loaded at from 30 g/L to 83 g/L and the physical mixture of Lewis acid catalyst and Bronsted acid catalyst is loaded at 30% to 100% with respect to the sugar loading.

5. The one-step process of claim 1, wherein the Lewis acid catalyst is selected from the group consisting of Sn-beta, $TiO_2$, $ZrO_2$, and $SnO_2$.

6. The one-step process of claim 1, wherein the Bronsted acid catalyst is selected from the group consisting of H-USY, H-beta, H-Y, H-ZSM-5, SBA-15, and combinations thereof.

7. The one-step process of claim 6, wherein the H-USY has a surface area from 600 m$^2$/g to 800 m$^2$/g and a Si:Al ratio from 12 to 30.

8. The one-step process of claim 1, wherein the alcohol is selected from the group consisting of C1 to C10 alcohols, methanol, ethanol, propanol, butanol, hexanol, octanol, and mixtures thereof.

9. The one-step process of claim 1, wherein the sugar is glucose, and wherein the platform chemicals comprise ethyl levulinate, 5-ethoxymethyl furfural, and ethyl lactate.

10. The one-step process of claim 9, wherein the Lewis acid catalyst is selected from the group consisting of Sn-beta, $TiO_2$, $ZrO_2$, and $SnO_2$, and the Bronsted acid catalyst is selected from the group consisting of H-USY, H-beta, H-Y, H-ZSM-5, SBA-15, and combinations thereof.

11. The one step-process of claim 10, wherein the physical mixture of the Lewis acid catalyst and the Bronsted acid catalyst has a strong to weak acidity ratio from 1.30 to 2.94, a Bronsted to Lewis acidity ratio from 0.60 to 0.75, and a total acidity from 0.64 mmol/g to 0.70 mmol/g.

12. The one-step process of claim 1, wherein the Lewis acid catalyst is selected from the group consisting of Sn-beta, $TiO_2$, $ZrO_2$, and $SnO_2$, and the Bronsted acid catalyst is selected from the group consisting of H-USY, H-beta, H-Y, H-ZSM-5, SBA-15, and combinations thereof.

13. The one-step process of claim 1, wherein the reaction product yield is from 80% to 85%.

14. The one-step process of claim 1, wherein the reaction time is from 0.5 h to 3 h.

15. The one-step process of claim 1, wherein the temperature is from 170° C. to 180° C.

16. The one-step process of claim 1, wherein:
the reaction time is from 0.5 h to 5 h;
the temperature is from 170° C. to 180° C.; and
the physical mixture of the Lewis acid catalyst and the Bronsted acid catalyst has a strong to weak acidity ratio from 1.30 to 2.94, a Bronsted to Lewis acidity ratio from 0.60 to 0.75, and a total acidity from 0.64 mmol/g to 0.70 mmol/g.

17. The one-step process of claim 16, wherein the sugar is glucose, and wherein the platform chemicals comprise ethyl levulinate, 5-ethoxymethyl furfural, and ethyl lactate.

18. A one-step process for converting sugars to platform chemicals, the one-step process comprising reacting a sugar with a physical mixture of a Lewis acid catalyst and a Bronsted acid catalyst at a temperature from 100° C. to 250° C. for 0.5 h to 7 h in an alcohol to obtain the platform chemicals with a reaction product yield from 60% to 85%, wherein the Bronsted acid catalyst and the Lewis acid catalyst in the physical mixture are present in a ratio of 95:5.

19. A one-step process for converting sugars to platform chemicals, the one-step process comprising reacting a sugar with a physical mixture of a Lewis acid catalyst and a Bronsted acid catalyst at a temperature from 100° C. to 250° C. for 0.5 h to 7 h in an alcohol to obtain the platform chemicals with a reaction product yield from 60% to 85%, wherein the physical mixture of the Lewis acid catalyst and the Bronsted acid catalyst has a strong to weak acidity ratio from 1.30 to 2.94, a Bronsted to Lewis acidity ratio from 0.60 to 0.75, and a total acidity from 0.64 mmol/g to 0.70 mmol/g.

20. The one-step process of claim 19, wherein:
   the sugar is glucose, and wherein the platform chemicals comprise ethyl levulinate, 5-ethoxymethyl furfural, and ethyl lactate;
   the Lewis acid catalyst is selected from the group consisting of Sn-beta, $TiO_2$, $ZrO_2$, and $SnO_2$;
   the Bronsted acid catalyst is selected from the group consisting of H-USY, H-beta, H-Y, H-ZSM-5, SBA-15, and combinations thereof.

* * * * *